United States Patent
Kirk et al.

[11] Patent Number: 5,138,124
[45] Date of Patent: Aug. 11, 1992

[54] APPARATUS FOR DESTROYING HYPODERMIC NEEDLES

[76] Inventors: William J. Kirk, 327 Gilbert Stuart Dr., East Greenwich, R.I. 02818; Stanley O. Thompson, 213 Jewett St., Providence, R.I. 02908; John G. Mathews, 154 Emeline St., Providence, R.I. 02906; William Lockett, III, 10A Cutters Green, North Providence, R.I. 02904; Richard A. Lynch, 206 Spring St., Cranston, R.I. 02910

[21] Appl. No.: 644,205
[22] Filed: Jan. 22, 1991
[51] Int. Cl.⁵ .............................. B23H 9/00
[52] U.S. Cl. .......................... 219/68; 83/944
[58] Field of Search ............ 219/68; 83/16, 944; 128/919; 241/65; 606/27

[56] References Cited
U.S. PATENT DOCUMENTS

| | | | |
|---|---|---|---|
| 4,628,169 | 12/1986 | Ch'ing-Lung | 219/68 |
| 4,877,934 | 10/1989 | Spinello | 219/68 |
| 4,961,541 | 10/1990 | Hashimoto | 219/68 |
| 4,965,426 | 10/1990 | Colombo | 219/68 |
| 5,046,669 | 9/1991 | Wallace et al. | 241/65 |

Primary Examiner—Geoffrey S. Evans
Attorney, Agent, or Firm—Wallenstein, Wagner & Hattis, Ltd.

[57] ABSTRACT

An apparatus for destroying used hypodermic needles includes a rotating electrode wheel, a stationary electrode element which is positioned in closely spaced relation to the electrode wheel and a guide member for guiding a hypodermic needle inserted into the apparatus so that it is advanced into electrical contact with the electrode wheel and the electrode element in order to electrically destroy the needle. The apparatus further includes a sensor for automatically energizing the electrode wheel and the electrode element when an operator approaches the apparatus, and a disposable cartridge assembly for receiving and containing debris generated as needles are destroyed in the apparatus.

22 Claims, 7 Drawing Sheets

APPARATUS FOR DESTROYING HYPODERMIC NEEDLES

BACKGROUND AND SUMMARY OF THE INVENTION

The instant invention relates to medical safety apparatus, and more particularly to an apparatus for destroying used hypodermic needles in order to minimize the risk of transmitting diseases to healthcare workers through inadvertent needle pricks. It has been found that annually a significant number of healthcare workers are infected with blood-borne diseases through inadvertent needle pricks from used hypodermic needles. It has been further found that although the likelihood of contracting a serious blood-borne disease through a single needle prick may be relatively small, the consequences can be extremely serious. In this connection, because needle pricks provide direct access to the venous systems of healthcare workers, it is possible for such workers to contract serious diseases, such as AIDS or hepatitis B through inadvertent needle pricks.

It has also been found that most needle pricks occur when used hypodermic needles are being prepared for disposal, although a certain number of needle pricks occur after disposal. In any event, because of the potentially serious consequences of needle pricks, there is a recognized need for an effective apparatus which eliminates both the need for handling used hypodermic needles to prepare them for disposal, as well as the need for handling used hypodermic needles after disposal.

The instant invention provides an effective apparatus for destroying used hypodermic needles immediately following use so that the risks associated with handling potentially contaminated hypodermic needles is minimized. More specifically, the instant invention provides an effective apparatus for electrically destroying hypodermic needles by instantaneously electrically heating them to temperatures in excess of the melting points of the metals from which they are constructed and for thereby converting used needles into relatively harmless powdered debris. The apparatus of the instant invention comprises a housing, a rotatable electrode wheel in the housing, means for rotating the electrode wheel, an electrode element located in closely spaced relation to the electrode wheel, and means for energizing the electrode wheel and the electrode element with a sufficient level of electrical current to cause the electrical destruction of a hypodermic needle positioned in electrical contact with both the electrode wheel and the electrode element. The electrode element is preferably constructed and mounted so that it remains substantially stationary during use of the apparatus, and the apparatus preferably further includes guide means for guiding a hypodermic needle inserted into the housing so that it passes into engagement with both the electrode wheel and the electrode element. The housing preferably has a needle entry opening therein, and the guide means is preferably operative for guiding a needle inserted into the housing through the needle entry opening. In addition, the apparatus preferably includes spark shield means in the needle entry opening for shielding an operator of the apparatus against sparks generated as a hypodermic needle is electrically destroyed in the housing. The spark shield means preferably includes a pair of resiliently yieldable spark shield elements, each of which has a pair of intersecting slits formed therein which are disposed in substantially perpendicular relation to each other. The two spark shield elements are preferably disposed in closely spaced substantially parallel relation to each other so that the intersections of the slits therein are substantially aligned but so that the slits in one spark shield element are at angles of approximately 45° with respect to the adjacent slits in the other spark shield element. The apparatus preferably still further includes filter means in the housing and fan means for drawing air inwardly into the housing through the needle entry opening so that the air passes around the electrode wheel and the electrode element and is then drawn through the filter means and exhausted from the housing. In addition, the apparatus preferably includes a cartridge in the housing which is operative for receiving debris generated when a needle is destroyed through contact with the electrode wheel and the electrode element. The cartridge preferably includes a container portion and a cover portion, and the container portion is preferably located in the housing so that it is operative for receiving debris generated as a hypodermic needle is destroyed through contact with the electrode wheel and the electrode element. The container portion of the cartridge preferably includes primary and secondary compartments, and the primary compartment is preferably operative for receiving debris, whereas the secondary compartment is preferably operative for receiving the cover portion of the cartridge in an inoperative position wherein the cover portion is removed from the upper end of the container portion. The apparatus preferably further includes a latch assembly on the housing which is operative for moving the cover portion to a retracted position wherein it is received in the secondary compartment as the cartridge is moved to an operative position in the housing. The latch assembly is preferably further operative for moving the cover portion to a position wherein it substantially covers the upper end of the container portion when the cartridge is removed from the housing. Still further, the apparatus preferably includes means for automatically actuating the means for rotating the electrode wheel and the means for energizing the electrode wheel and the electrode element when an operator approaches the apparatus to destroy a needle therewith. The automatic actuating means preferably comprises an infrared sensor on the housing which is operative for sensing a hand of an operator as the operator approaches the apparatus to dispose of a needle therein.

It has been found that the apparatus of the instant invention can be effectively utilized for destroying needles in order to minimize the risk to healthcare workers of needle pricks from contaminated needles. Specifically, it has been found that the apparatus of the instant invention can be effectively utilized for rapidly and completely destroying used needles. It has been further found that because the apparatus is adapted to be automatically actuated as healthcare workers approach the apparatus, it is further operative for minimizing the activities required to be performed by healthcare workers prior to destroying needles.

The closest prior art to the instant invention of which the applicant is aware is disclosed in the U.S. Pat. to Ch'Ing-Lung No. 4,628,169. However, the device disclosed in this reference fails to include a rotating electrode wheel such as found in the apparatus of the instant invention, as well as many of the other components of the apparatus of the instant invention, and hence the U.S. Pat. to Ch'Ing Lung is believed to be of only general interest with respect to the instant invention.

Accordingly, it is a primary object of the instant invention to provide an effective apparatus for destroying used hypodermic needles.

Another object of the instant invention is to provide an apparatus which is conveniently operable by healthcare workers for destroying hypodermic needles immediately following use.

Another object of the instant invention is to provide an apparatus which is operative for reducing the risk of transmitting infectious diseases to healthcare workers through inadvertent needle pricks. Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Referring now to the drawings, the apparatus of the instant invention is illustrated in FIGS. 1 through 9 and generally indicated at 10 in FIGS. 1-8. The apparatus 10 comprises a housing assembly generally indicated at 12, a rotatable electrode wheel generally indicated at 14, a drive assembly generally indicated at 18, a transformer assembly generally indicated at 20, a controller assembly generally indicated at 22, a cartridge assembly generally indicated at 24, and a spark shield assembly generally indicated at 26. The electrode wheel 14 is rotatably mounted in the housing assembly 12, and the fixed electrode element 16 is mounted in the housing 12 in closely spaced relation to the electrode wheel 14. During operation of the apparatus 14, the drive assembly 18 is operative for rotating the electrode wheel 14, and the transformer assembly 20 is operative for energizing the electrode wheel 14 and the electrode element 16 so as to produce an electrical potential therebetween. The apparatus 10 is operative by inserting a hypodermic needle 27 attached to a syringe 27a through the spark shield assembly 26 so that the needle 27 contacts both the electrode element 16 and the electrode wheel 14 in order to electrically destroy the needle 27. The cartridge assembly 24 is operative for receiving particles of debris 27b generated as the needle 27 is destroyed, and it is removable from the housing assembly 12 for safe disposal.

The housing assembly 12 comprises top and bottom housing sections 28 and 30, respectively, and an inner drive housing member 32, each of which is preferably integrally molded from a suitable plastic, and the housing assembly 12 further comprises an inner electrode housing member 34. The upper housing section 28 has a needle entry opening 36 formed therein, and the spark shield assembly 26 is received in the opening 36. An angularly disposed wall 38 is integrally formed in the upper housing section 28 adjacent the needle entry opening 36, and an infrared sensor 40 which is part of the control assembly 22 is mounted on the wall 38 adjacent the needle entry opening 36. The upper and lower housing sections 28 and 30, respectively, are preferably formed so that they cooperate to define a housing which is operative for containing the operative components of the apparatus 10, but which is open at one end thereof for receiving the cartridge assembly 24 in a manner which will hereinafter be more fully set forth. Integrally formed in the interior of the lower housing section 30 is a plurality of partitions and other structural walls which are specifically adapted to provide effective and convenient means for positioning and securing the drive assembly 18, the transformer assembly 20, and the control assembly 22 in the housing assembly 12. These partitions and structural walls include a fan housing section 42, a motor mount section 44., and a transformer partition 46. The fan housing section 42 cooperates with the internal drive assembly housing 32 to provide a housing for a fan portion of the drive assembly 18, as will hereinafter be more fully set forth. The motor mount section 44 and the transformer partition 46 are operative for mounting a motor portion of the drive assembly 18 and the transformer assembly 20, respectively, in the lower housing section 30.

The inner drive housing member 32 is dimensioned and configured so that it cooperates with the lower housing section 30 to substantially enclose the main portions of the drive assembly 18. Included in the inner drive housing member 32 is a plurality of upstanding locating fingers 48 which are operative for locating the inner electrode housing member 34 during assembly of the apparatus 10. The inner drive housing member 32 is further operative for rotatably mounting the electrode wheel assembly 14 in the housing 12 as illustrated.

The inner electrode housing member 34 is dimensioned and configured to be received in the housing sections 28 and 30 so that it extends over the electrode wheel 14 and the electrode element 16. The inner electrode housing member 34 includes a housing portion 50 and a needle guide member 52. The housing portion 50 is preferably integrally molded from a suitable plastic material, and it has a plurality of slots (not shown) therein which are operative for receiving the fingers 48 in order to position the electrode housing member 3 in the lower housing section 30 during assembly of the apparatus 10. The housing portion 50 includes a tubular shaft support member 54 which is positioned for receiving a shaft of the rotatable electrode wheel assembly 14 therein. The needle guide member 52 is preferably made from a suitable metal, such as aluminum or stainless steel, and it has a concave entry surface 56 formed therein which merges into a central needle entry opening 58. As illustrated most clearly in FIGS. 4 and 5, the needle entry opening 58 is located directly above the electrode wheel assembly 14 and the electrode element 16 so that the guide member 52 is operative for guiding a needle 27 into contact with the electrode wheel 14 and the electrode element 16.

The electrode wheel assembly 14 comprises a drive shaft 60 having a drive pulley 62 thereon, and an electrode wheel 64, and a heat sink wheel 66 which are also mounted on the shaft 60. The drive shaft 60 is made from a suitable conductive metal, and it is rotatably mounted on the inner drive assembly housing member 32 and the inner electrode assembly housing member 34. The drive pulley 62 preferably comprises a multi-toothed drive pulley, and it is mounted on the shaft 60 for rotating the electrode wheel 64 and the heat sink wheel 66. The electrode wheel 64 is made from a suitable conductive metal such as brass, tungsten, or molybdenum. The heat sink wheel 64 has a substantially cylindrical outer circumferential surface although it has a plurality of grooves 68 formed therein. The heat sink wheel 66 is mounted on the shaft 60 in closely spaced relation to the electrode wheel 64, and it is formed as a gear-shaped wheel in order to increase the amount of surface area available for dissipating heat from the electrode wheel assembly 14.

The electrode element 16 comprises a metal band which is preferably made of a metal, such as brass, tungsten, or molybdenum. The electrode element 16 is mounted on the electrode assembly housing section 34 so that it extends to a point which is closely spaced from the upper side of the electrode wheel 64 as illustrated most clearly in FIGS. 4 and 5. The electrode element 16 is preferably at least slightly resiliently flexible to allow it to flex downwardly as a needle is destroyed in the apparatus 10 so that substantially the entire needle can be destroyed up to the mounting hub thereof. However, the electrode element must nevertheless be sufficiently rigid to maintain the free end thereof in closely spaced relation to the electrode wheel 64 without actually contacting the electrode wheel 64.

Figure 1:
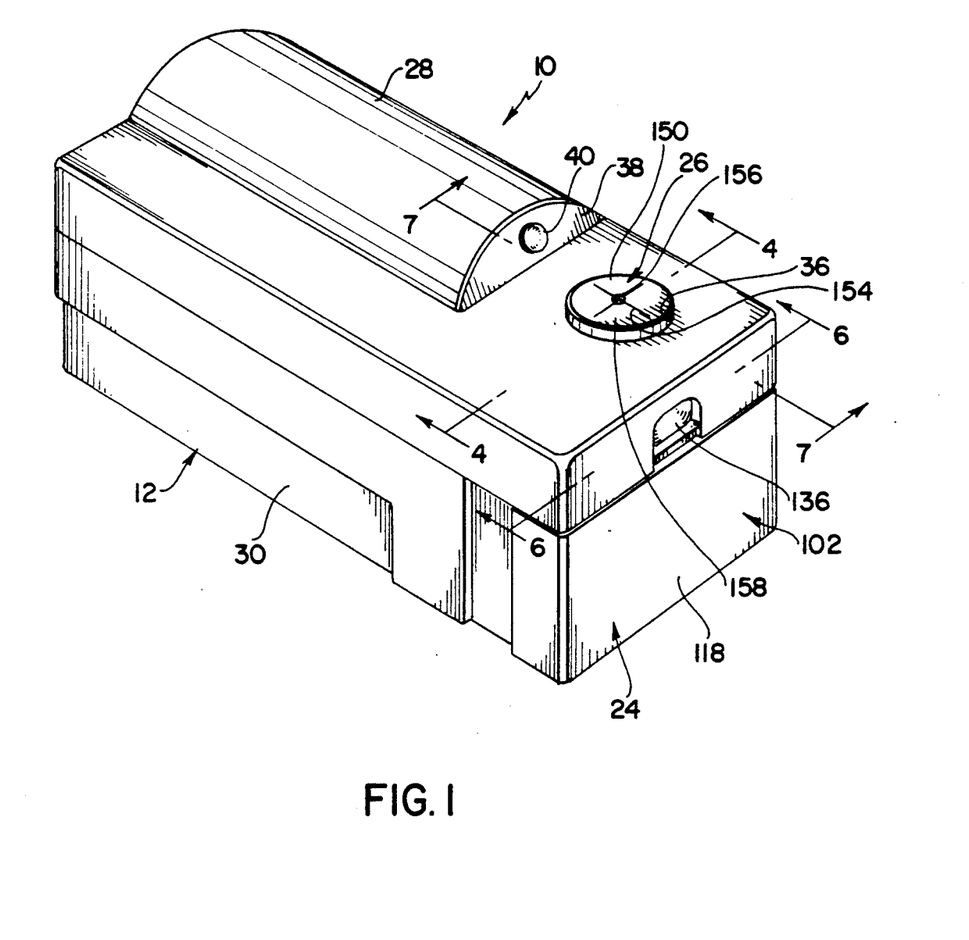
FIG. 1 is a perspective view of the apparatus of the instant invention.
Figure 2:
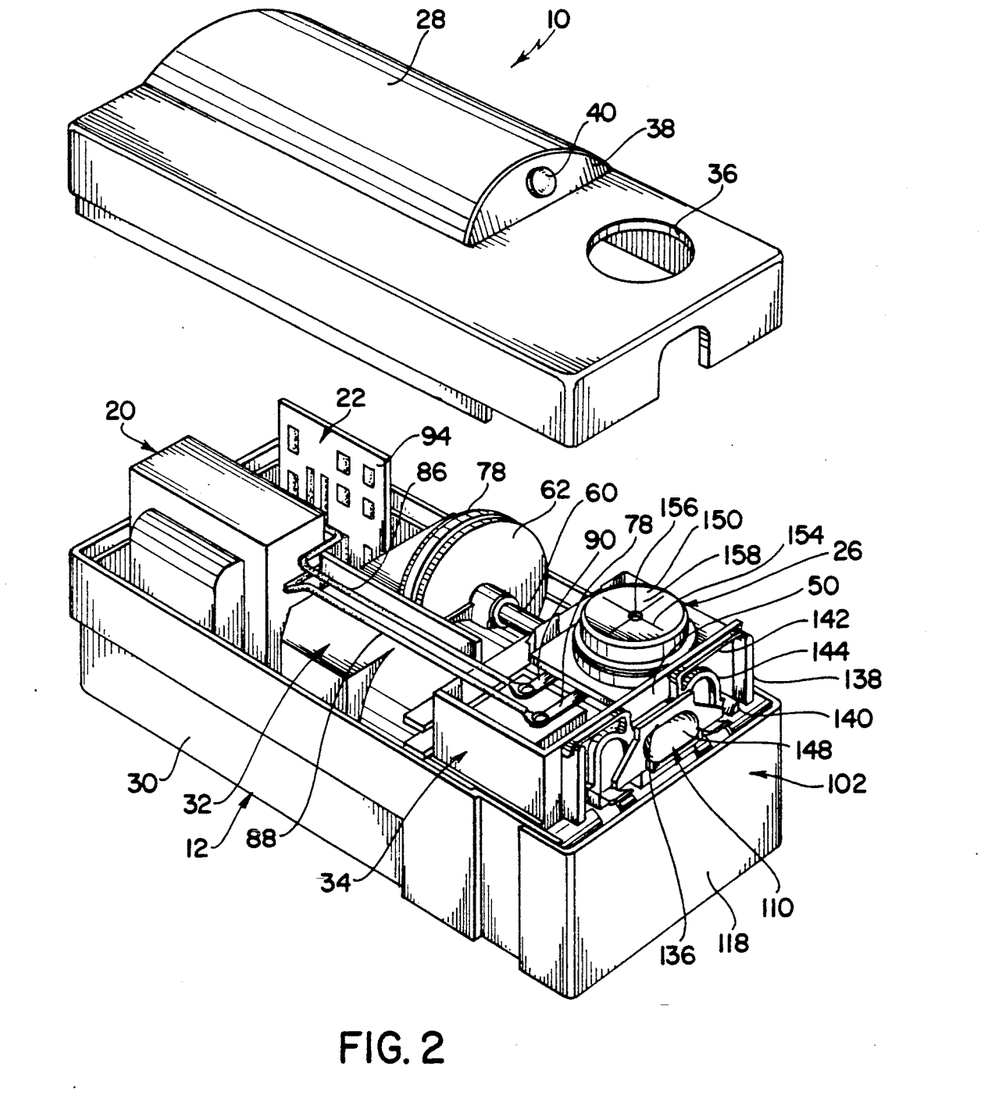
FIG. 2 is a perspective view thereof with the cover portion of the housing removed.
Figure 3:
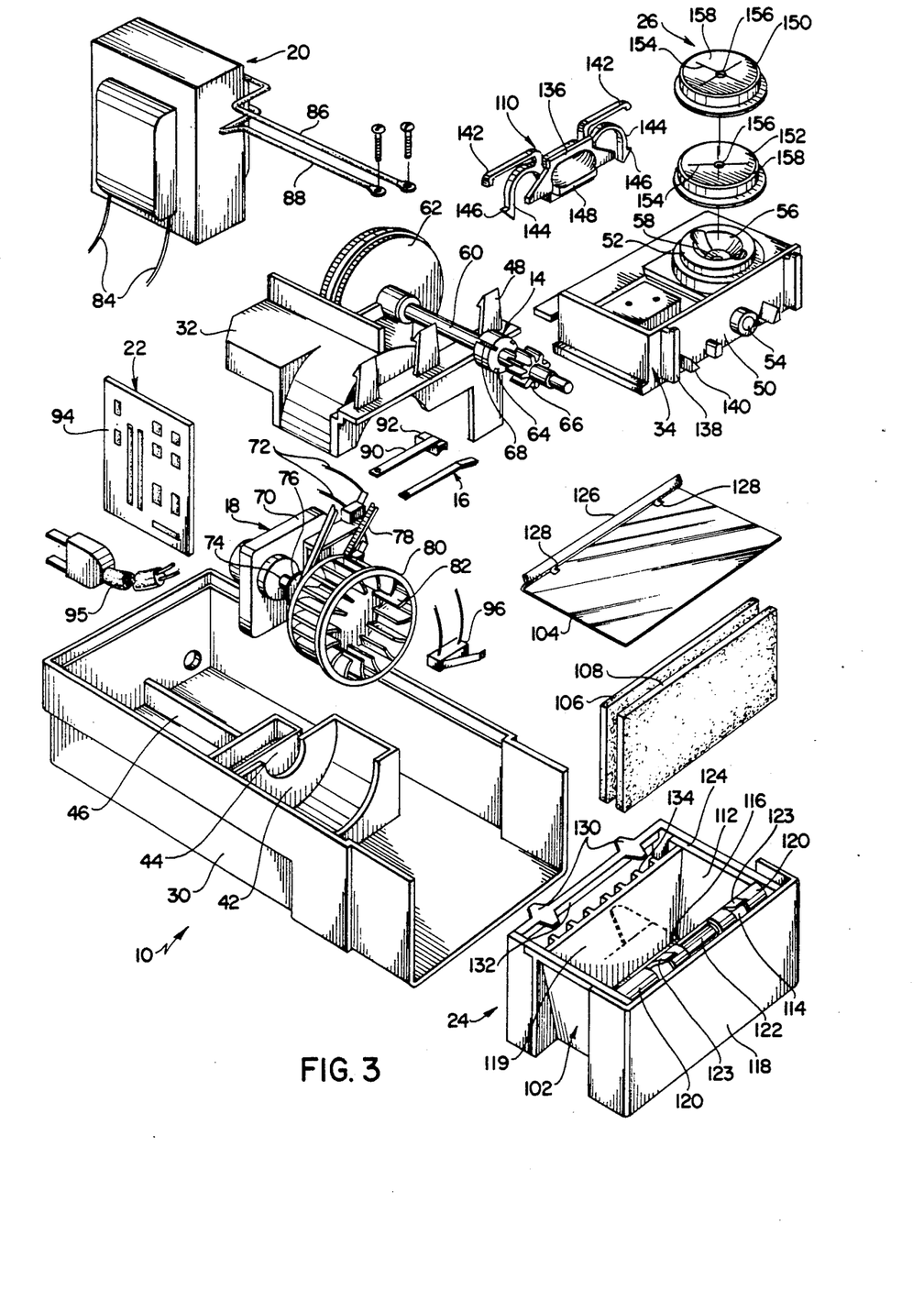
FIG. 3 is an exploded perspective view thereof without the cover portion of the housing.
Figure 4:
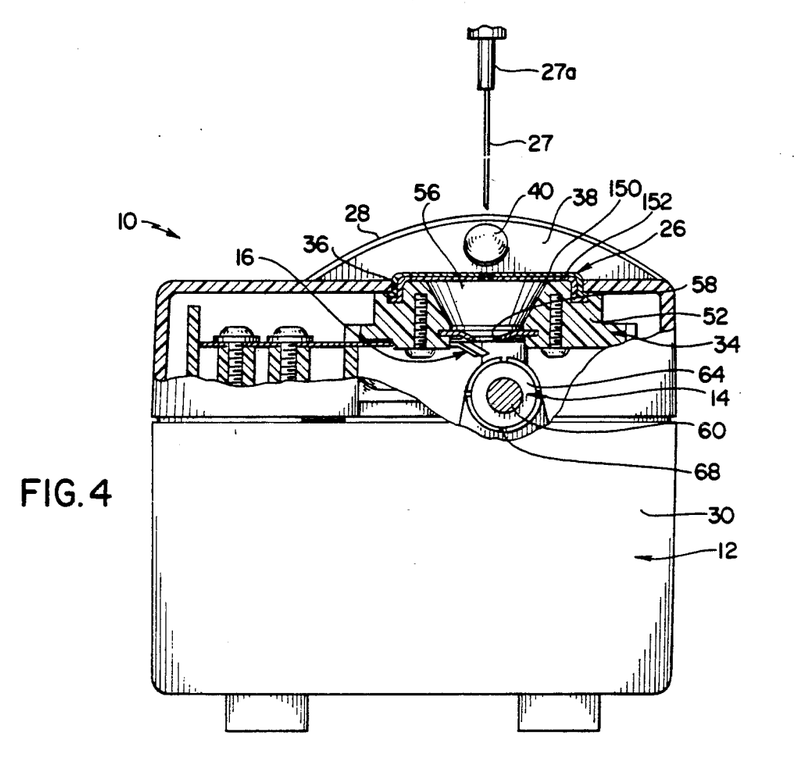
FIGS. 4 and 5 are end elevational views shown in partial section illustrating the destruction of a needle in the apparatus.
Figure 5:
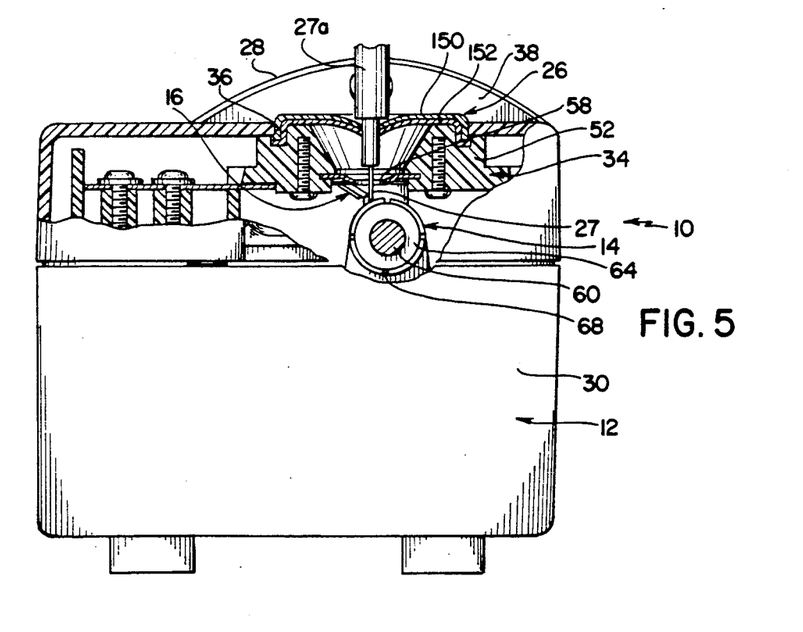
Figure 6:
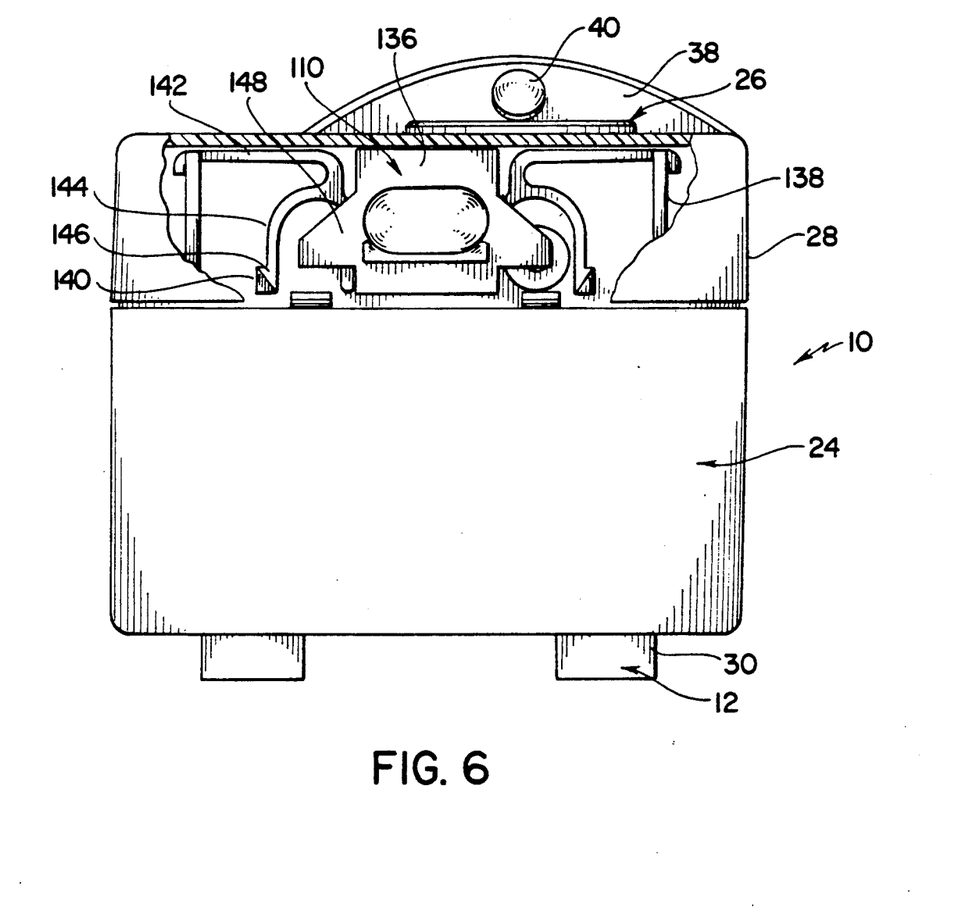
FIG. 6 is an end elevational view shown in partial section illustrating the latch assembly.
Figure 7:
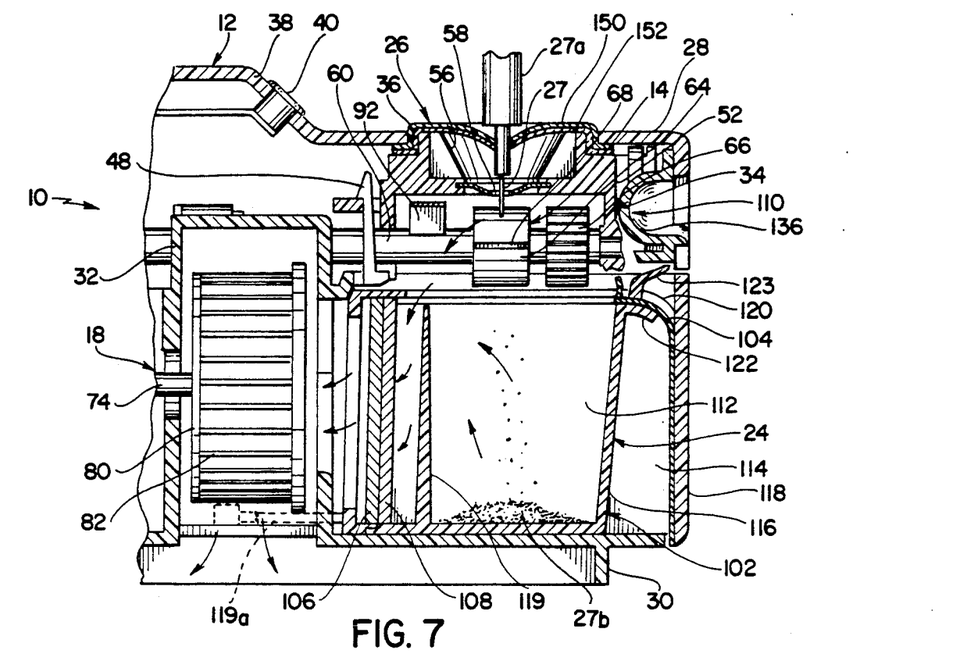
FIG. 7 is a fragmentary front sectional view illustrating the operation of the apparatus for destroying a needle.
Figure 8:
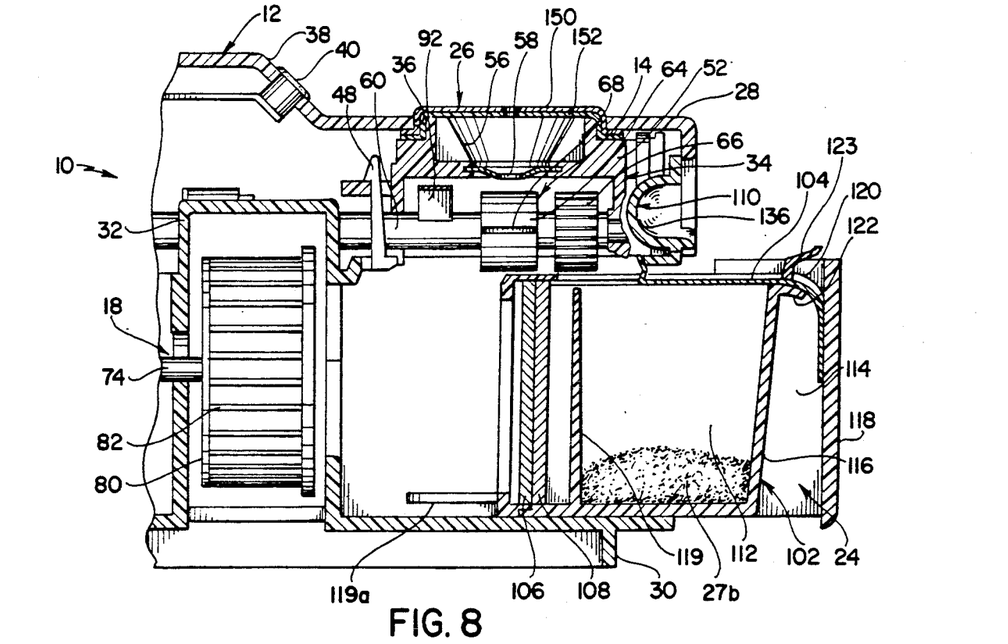
FIG. 8 is a fragmentary front sectional view illustrating the operation of the cartridge assembly.

The drive assembly 18 is illustrated most clearly in FIGS. 3, 7 and 8, and it includes a drive motor 70 which is energizable through wires 72 and a drive shaft 74, a drive pulley 76, a drive belt 78, and a fan 80. The drive motor 70 is mounted in the lower housing section 30 so that it is received in the motor mounting member 44, and the pulley 76 and the fan 80 are mounted on the drive shaft 74 so that the fan 80 is positioned in the fan housing section 42. The pulley 76 preferably comprises a multi-toothed pulley, and the drive belt 78, which preferably has corresponding teeth formed on the inner surface thereof, extends between the pulley 76 and the pulley 62 for rotating the shaft 60 to drive the electrode wheel 64. The fan 80 comprises a circular cage-type fan which includes a plurality of veins 82, and it is operative for drawing a vacuum in the interior of the housing 12 so that air is drawn inwardly through the needle entry opening 58 and then circulated around the electrode wheel 64 and the fixed electrode element 16 before passing through a filter in the cartridge assembly 24 and into the fan 80. Air from the fan 80 is exhausted from the housing 12 through an exhaust opening (not shown) located in the bottom wall of the lower housing section 30.

The transformer assembly 20 comprises a conventional transformer, and it is preferably operative for producing an output voltage of between 2 and 3 volts AC. The transformer assembly 20 is preferably capable of generating in excess of 100 amps of output current for short periods of time. The transformer is energized through input wires 84, and it includes first and second output wires 86 and 88, respectively. The transformer 20 is mounted in the lower housing section 30 so that it is contained by the partition 46, and the first output wire 86 extends to a brush member 90 comprising an electrical brush element 92 which is biased to a position of engagement with the shaft 60 for energizing the electrode wheel 64. The second output wire 88 from the transformer 20 is connected to the fixed electrode element 16. Accordingly, the transformer assembly 20 is operative for producing a voltage of between 2 and 3 volts across the electrode wheel 64 and the electrode element 16 and for passing an electrical current of up to 100 amps therebetween when a hypodermic needle is placed in engagement with both the electrode wheel 64 and the electrode element 16.

Figure 9:
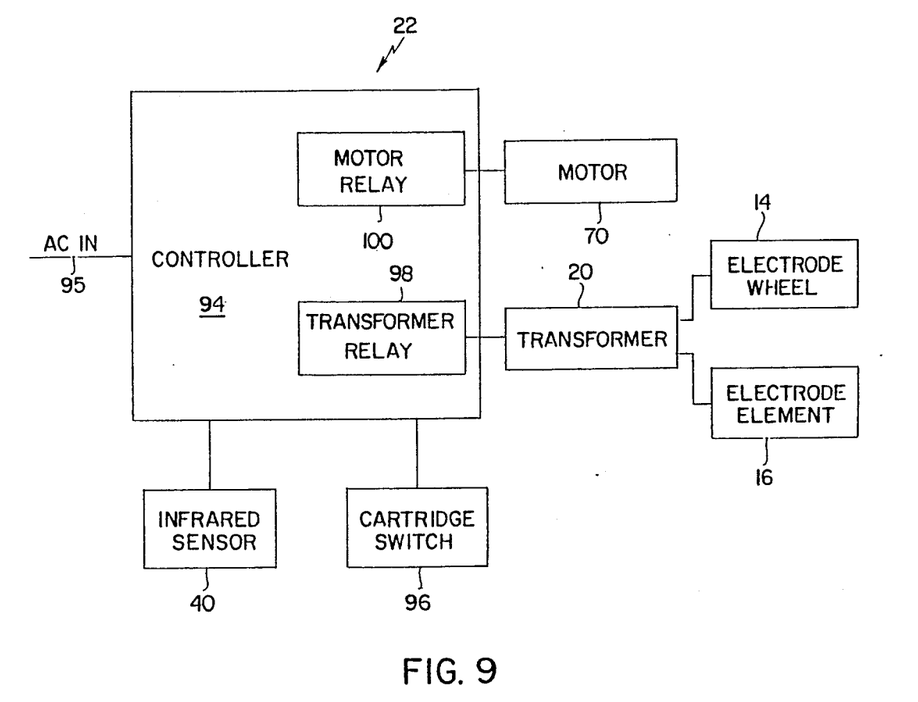
FIG. 9 is a schematic block diagram of the controller of the apparatus.

The control assembly 22 is schematically illustrated in FIG. 9, and it includes a controller or control circuit 94 which is mounted in the lower housing section 30, a power cord 95, the infrared sensor 40, and a cartridge switch 96. The infrared sensor 40 is of conventional construction, and it is operative for sensing the presence of heat, such as the heat generated by a human hand, in the area of the needle entry opening 36. The cartridge switch 96 is mounted on the bottom wall of the lower housing section 30, and it is operative for sensing whether or not the cartridge assembly 24 is in an operative position in the housing 12. The controller 94, which is connected to the power cord 95, includes a transformer relay 98 and a motor relay 100. The controller 94 comprises a conventional switching circuit which is responsive to signals from the infrared sensor 40 for energizing the transformer relay 98 and the motor relay 100 when the presence of a human hand in the proximity of the needle entry opening 36 is detected by the infrared sensor 40, and it is responsive to the cartridge switch 96 for de-actuating the motor relay 100 and the transformer relay 98 in the event that the cartridge assembly 24 is not in an assembled operative position in the housing 12. However, when the transformer relay 98 and the motor relay 100 are actuated, AC power is supplied to the motor 70 and the transformer 20 in order to render the apparatus 10 operative.

The cartridge assembly 24 is illustrated most clearly in FIGS. 3 and 6 through 8, and it includes a container member 102, a cover member 104, first and second filter elements 106 and 108, respectively, and a latch assembly 110. The container member 102 includes primary and secondary compartments 112 and 114, respectively, which are segregated by a partition 116. An outer end wall 118 which is in closely spaced, substantially parallel relation to the partition 116 defines the outer end of the container member 102, and an inner end wall 119 having a switch actuator tab 119a adjacent the lower end thereof is also included in the container member 102. A plurality of arcuate guide members 120 extend upwardly and inwardly from the outer wall 118 in slightly downwardly spaced relation to the upper end thereof. A corresponding guide member 122 extends downwardly and outwardly from the upper extremity of the partition 116, and a pair of latch tongues 123 extend upwardly and outwardly from the partition 116. The cover member 104 is preferably constructed from a resiliently flexible plastic material, and it is constructed so that it is receivable in the secondary compartment 114 of the container member 102 when the cartridge assembly 24 is in an open operative position and so that the cover member 104 is received in covering relation on the container member 102 when the cartridge assembly 24 is in a closed position. In this connection, the guide members 120 and 122 are operative for guiding the cover member 104 as it is moved between the open and closed positions thereof, and tracks 124 extend along the opposite side extremities of the container member 102 adjacent the upper end thereof for further guiding the cover member 104 and for retaining it in substantially covering relation on the container member 102 when the cover member 104 is in the closed position thereof. An upturned lip 126 extends along on edge of the cover member 124, and a pair of spaced slots 128 are formed in the cover member 102 adjacent the lip 126. A pair of tabs 130 are provided on a cross member 132 on the container member 102 which extends along the upper extremity of the container member 102 in slightly rearwardly spaced relation to the partition 119 as illustrated. The tabs 130 are receivable in the slots 128 in the cover member 104 to retain the cover member 104 in the closed position thereof. Further, when the cartridge assembly 24 is received in an operative position in the housing 12, the tab 119a engages the switch 96 to enable the controller to energize the motor 70, the electrode element 16 and the electrode wheel assembly 14. The filter element 106 preferably comprises an activated charcoal type filter element, and the filter element 108 preferably comprises a wire screening type filter element. The filter elements 106 and 108 are preferably laminated together, and they are received on the outer side of the partition 119. In this connection, a plurality of spacer members 134 are provided on the outer surface of the partition 119, and the filter elements 106 and 108 are received along the spacer elements 134 so that they are retained in position by the cross member 132 and the tabs 130. The filter elements 106 and 108 are positioned so that air escaping from the primary compartment 112 of the container member 102 must pass through the filter elements 106 and 108 in order to exit between the cross member 132 and the partition 119. As illustrated in FIG. 7, when the cartridge member 24 is received in the housing 12, the cartridge 24 abuts against the fan housing section 42 and the drive assembly housing section 32 so that the fan 80 is operative for drawing air through the filter elements 106 and 108. Further, in order for air to be drawn through the filter elements 106 and 108 with the fan 80 the air must either enter through the needle entry opening 58 or through various joints in the housing assembly 12. In any event, substantially all of the air passing through the filter elements 106 and 108 must pass around the electrode wheel 64 and the electrode element 16 so that any gases generated as hypodermic needles are electrically destroyed through contact with the electrode element 16 and the electrode wheel 64 are drawn through the filter elements 106 and 108 with the fan 80.

The latch assembly 110 includes a latch member 136, which is operative in combination with a pair of support members 138 and a pair of angular cam members 140 on the outwardly facing side of the electrode assembly housing member 34. The latch member 136 includes a pair of resilient support arms 142 which are receivable on the support members 138 for supporting the latch member 136 on the electrode housing member 34. The latch member 136 further includes a pair of resilient latch arms 144 having latches 146 thereon. The latch member 136 further includes a central portion 148 from which the latch arms 144 and the support arms 142 extend. The latch member 136 is movable between a downwardly disposed release position wherein the latch arms 144 are cammed inwardly and downwardly so that the latches 146 are received beneath the cam elements 140 and a locked position wherein the latches 146 are positioned along the angular inwardly facing surfaces of the cam members 140 and wherein the central portion 148 is held upwardly by the support arms 142. When the cartridge assembly 24 is in an operative position wherein it is fully received in the housing 12, the latch member 136 is normally located in the upper locked position thereof, wherein the latch tongues 123 are received inwardly of the lower edge of the upper housing section 28 to prevent the cartridge assembly 24 from being removed from the housing assembly 12. However, by depressing the latch member 136 downwardly, the latch tongues 123 can be deflected downwardly to permit the cartridge assembly 24 to be removed from the housing assembly 12. When the latch member 136 is moved downwardly in this manner, the latch arms 144 are cammed inwardly and together until the latches 146 are received past the cam elements 140 to retain the latch member 136 in the downwardly disposed release position. When the latch member 136 is in this position, the central portion 148 engages the upwardly extending lip 126 on the cover member 104 to draw the cover member 104 into covering relation on the container member 102 as the cartridge assembly 24 is removed from the housing assembly 12. In this connection, when the cartridge assembly 24 is disposed in an operative position in the housing assembly 12, the cover member 104 is normally located in the secondary compartment 114. However, because the central portion 148 of the latch member 136 engages the lip 126 of the cover member 104, the cover member 104 is automatically drawn to a covering position on the container member 102 as the cartridge assembly 24 is removed from the housing assembly 12. When the lip 126 of the cover member 104 reaches the tabs 130 as the cartridge assembly 24 is removed from the housing assembly 12, the tabs 130 are received in the slots 128 in the cover member 104. Further, as the tabs 130 are received in the slots 128, they operate to disengage the latches 146 from the cam members 140 so that the latch member 136 is resiliently returned to an upwardly disposed locked position. However, when a new cartridge assembly 24 is assembled with the housing assembly 12, the lip 126 of the cover member 104 of the new cartridge assembly 24 engages the outwardly facing wall of the electrode assembly housing member 34 to move the cover portion 104 of the new cartridge assembly 24 to an open position wherein it is received in the secondary chamber 114 of the container portion 102 thereof. As the new cartridge assembly 24 is assembled with the housing assembly 12 in this manner, the latch tongues 123 of the new cartridge assembly 24 are resiliently deflected downwardly so that they pass beyond the lower edge of the upper housing section 28 to retain the new cartridge assembly 24 in the housing assembly 12

The spark shield assembly 26 comprises upper and lower spark shield elements 150 and 152, respectively, which are preferably constructed from a resiliently flexible high-temperature resistant plastic, such as a silicone plastic. The spark shield elements 150 and 152 each have a pair of substantially perpendicularly disposed slits 154 formed therein which intersect at a central point 156. The slits 154 define resiliently deflectable segments 158 which are deflectable downwardly as a hypodermic needle is inserted into the apparatus 10.

The spark shield elements 150 and 152 are coaxially positioned with respect to each other, but they are oriented so that the slits 154 in the upper spark shield element 150 are at angles of approximately 45° with respect to the adjacent slits in the lower spark shield element 152. As a result, the spark shield elements 150 and 152 are able to more effectively cooperate to prevent sparks from reaching a hand of an operator as a hypodermic needle is inserted through the openings 156 and 58.

During use and operation of the apparatus 10 for destroying a needle 27, as the needle 27 approaches the spark shield assembly 26, the infrared sensor 40 detects the proximity of a hand of the operator to actuate the controller 94 for energizing the motor 70 and the transformer 20. As the needle 27 is advanced through the openings 156 in the spark shield elements 150 and 152, the segments 158 of the spark shield elements are deflected downwardly slightly, and the needle 27 is guided into the opening 58 by the needle guide surface 56. As the needle 27 is passed downwardly through the opening 58 it comes into contact with the electrode element 16 and the electrode wheel 64 to produce a short circuit therebetween. As a result, the needle 27 is immediately heated to a temperature above the melting point thereof and turned into a powdered debris 27b which falls into the primary compartment 112 of the container portion 102 of the cartridge assembly 24. As the needle 27 is further advanced downwardly, sequential portions thereof are destroyed through contact with the electrode element 16 and the electrode wheel 64. Further, the transverse slits 68 in the electrode wheel 64 cause slag formed as the needle 27 is melted to be removed from the needle 27 and passed into the container portion 102. During this procedure, the fan 80 acts to draw gases generated as the needle 27 is destroyed through the filter elements 106 and 108 so that essentially pure air is exhausted from the housing 12 with the fan 80. When the container portion 102 becomes filled with debris 27b from needles 27 disposed of in this manner, the latch member 136 can be moved downwardly to disengage the latch tongues 123 from the bottom edge of the upper housing section 28. As the latch member 136 is moved downwardly, the latches 146 pass over the cam elements 140 so that the latch member 136 is retained in a downwardly disposed position. As a result, as the cartridge member 24 is removed from the housing assembly 12, the latch member 148 engages the lip 126 of the cover portion 104 to draw the cover portion 104 over the upper end of the container portion 102 to effectively move the cartridge assembly 24 to a closed position. When the cover portion 104 reaches a fully closed position on the container portion 102, the tabs 130 are received in the slots 128, and the tabs 30 then engage the latches 146 to release them from the cam members 140 so that the latch member 136 is released to an upwardly disposed locked position. When a new cartridge assembly 24 is then inserted into the housing assembly 12, the cover portion 104 of the new cartridge assembly 24 is moved to an open position as the new cartridge assembly 24 is advanced into the housing assembly 12 in the manner hereinabove set forth.

It is seen therefore that the instant invention provides an effective apparatus for destroying hypodermic needles 27. The apparatus 10 includes an electrode wheel 64 and an electrode element 16 which effectively cooperate to destroy a hypodermic needle 27 positioned in electrical contact therewith. The apparatus 10 further includes means for filtering gases generated during the destruction of a needle 27, means for effectively shielding the hands of an operator from sparks generated during the destruction of a needle 27 and means for automatically actuating the transformer 20 and the motor 70 when an operator approaches the apparatus 10. Further, the apparatus 10 includes an effective cartridge assembly 24 which is automatically moved to a closed position as it is removed from the housing assembly 12. Accordingly, it is seen that the apparatus of the instant invention represents a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. An apparatus for destroying hypodermic needles comprising:
    (a) a rotatable electrode wheel;
    (b) means for rotating said electrode wheel;
    (c) a substantially fixed electrode element, said electrode element being disposed in closely spaced relation to said electrode wheel; and
    (d) means for energizing said electrode wheel and said electrode element with a sufficient level of electrical current to cause the electrical destruction of a hypodermic needle positioned in electrical contact with both said electrode wheel and said electrode element.

2. The apparatus of claim 1, further comprising guide means for guiding a hypodermic needle approaching said electrode wheel so that it passes into engagement with both said electrode wheel and said electrode element.

3. The apparatus of claim 2, further comprising spark shield means for shielding an operator inserting a needle through said guide means against sparks generated as said needle is destroyed as it contacts said electrode wheel and said electrode element.

4. In the apparatus of claim 3, said spark shield means comprising a pair of resiliently yieldable spark shield elements, each of said spark shield elements being made of a resiliently flexible sheet material and having a pair of intersecting slits therein which are disposed in substantially perpendicular relation to each other, said spark shield elements being disposed in closely spaced, substantially parallel relation so that the intersections of the slits therein are substantially aligned but so that the slits in one spark shield element are at angles of approximately 45° with respect to the adjacent slits in the other spark shield element.

5. The apparatus of claim 2, further comprising a housing having a needle entry opening therein, said electrode wheel, said electrode element and said guide means being located in said housing, said guide means being operative for guiding a needle longitudinally inserted into said needle entry opening so that it passes into engagement with both said electrode wheel and said electrode element.

6. The apparatus of claim 5 further comprising filter means and fan means in said housing, said fan means being operative for withdrawing air from around said electrode wheel and said electrode element so that the withdrawn air passes through said filter means and is then exhausted from said apparatus.

7. The apparatus of claim 5 further comprising cartridge means in said housing, said cartridge means being normally received in an operative position in said housing wherein said cartridge means is operative for receiving debris generated when a needle is destroyed through contact with said electrode wheel and said electrode element, said cartridge means being removable from said housing and being self-closing to contain said debris therein upon removal of said cartridge means from said housing.

8. The apparatus of claim 7, further comprising switch means for deactuating said means for energizing said electrode wheel and said electrode element in the event that said cartridge means is not in the operative position thereof.

9. The apparatus of claim 5, further comprising cartridge means in said housing, said cartridge means including a container portion and a cover portion, said container portion being operative for receiving debris generated through contact with said electrode wheel and said electrode element, said cartridge means being removable from said apparatus, said cartridge means being adapted so that said cover portion is automatically received on said container portion upon removal of said cartridge means from said housing.

10. In the apparatus of claim 9, said container portion having an open upper end and having primary and secondary compartments formed therein, said primary compartment being operative for receiving said debris therein, said cover portion being retracted into said secondary compartment when said cartridge means is in the operative position thereof and substantially covering the upper end of said container portion when said cartridge means is removed from said housing.

11. The apparatus of claim 10, further comprising latch means on said housing for moving said cover portion to a retracted position wherein said cover portion is received in said secondary compartment when said cartridge means is moved to the operative position thereof and for moving said cover portion to a position wherein said cover portion substantially covers the upper end of said container portion when said cartridge means is removed from said housing.

12. The apparatus of claim 1, further comprising a housing with filter means and fan means in said housing, said fan means being operative for drawing air inwardly into said housing through said needle entry opening so that it passes by said electrode wheel and said electrode element, then through said filter element and is then exhausted from said housing.

13. The apparatus of claim 1, further comprising means for automatically actuating said means for rotating said electrode wheel and said means for energizing said electrode wheel and said electrode element when an operator approaches said apparatus to destroy a needle therewith.

14. In the apparatus of claim 13, said means for automatically actuating comprising an infrared sensor.

15. An apparatus for destroying hypodermic needles comprising:
a rotatable electrode wheel;
means for rotating said electrode wheel;
an electrode element, said electrode element being disposed in closely spaced relation to said electrode wheel;
means for energizing said electrode wheel and said electrode element with a sufficient level of electrical current to cause the electrical destruction of a hypodermic needle positioned in electrical contact with both said electrode wheel and said electrode element; and
means for automatically actuating said means for rotating said electrode wheel and said means for energizing said electrode wheel and said electrode element when an operator approaches said apparatus to destroy a needle therewith.

16. In the apparatus of claim 15, said means for automatically actuating comprising an infrared sensor.

17. An apparatus for destroying hypodermic needles comprising:
a rotatable electrode wheel;
means for rotating said electrode wheel;
an electrode element, said electrode element being disposed in closely spaced relation to said electrode wheel;
means for energizing said electrode wheel and said electrode element with a sufficient level of electrical current to cause the electrical destruction of a hypodermic needle positioned in electrical contact with both said electrode wheel and said electrode element;
a housing have a needle entry opening therein, said electrode wheel, said electrode element and said guide means being located in said housing, said guide means being operative for guiding a needle longitudinally inserted into said needle entry opening so that it passes into engagement with both said electrode wheel and said electrode element; and
filter means and fan means in said housing, said fan means being operative for withdrawing air from around said electrode wheel and said electrode element so that the withdrawn air passes through said filter means and is then exhausted from said apparatus.

18. An apparatus for destroying hypodermic needles comprising:
a rotatable electrode wheel;
means for rotating said electrode wheel;
an electrode element, said electrode element being disposed in closely spaced relation to said electrode wheel;
means for energizing said electrode wheel and said electrode element with a sufficient level of electrical current to cause the electrical contact with both said electrode wheel and said electrode element; and
filter means and fan means in said housing, said fan means being operative for drawing air inwardly into said housing through said needle entry opening so that it passes by said electrode wheel and said electrode element, then through said filter element and is then exhausted from said housing.

19. An apparatus for destroying hypodermic needles comprising:
a rotatable electrode wheel;
means for rotating said electrode wheel;
an electrode element, said electrode element being disposed in closely spaced relation to said electrode wheel;
means for energizing said electrode wheel and said electrode element with a sufficient level of electrical current to cause the electrical destruction of a hypodermic needle positioned in electrical contact with both said electrode wheel and said electrode element;

guide means for guiding a hypodermic needle approaching said electrode wheel so that it passes into engagement with both said electrode wheel and said electrode element; and spark shield means for shielding an operator inserting a needle through said guide means against sparks generated as said needle is destroyed at it contacts said electrode wheel and said electrode element, wherein said spark shield means comprises a pair of resiliently yieldable spark shield elements, each of said spark shield elements being made of a resiliently flexible sheet material and having a pair of intersecting slits therein which are disposed in substantially perpendicular relation to each other, said spark shield elements being disposed in closely spaced, substantially parallel relation so that the intersections of the slits therein are substantially aligned but so that the slits in one spark shield element are at angles of approximately 45° with respect to the adjacent slits in the other spark shield element.

20. An apparatus for destroying hypodermic needles comprising:

a rotatable electrode wheel;

means for rotating said electrode wheel;

an electrode element, said electrode element being disposed in closely spaced relation to said electrode wheel;

means for energizing said electrode wheel and said electrode element with a sufficient level of electrical current to cause the electrical destruction of a hypodermic needle positioned in electrical contact with both said electrode wheel and said electrode element;

guide means for guiding a hypodermic needle approaching said electrode wheel so that it passes into engagement with both said electrode wheel and said electrode element;

a housing have a needle entry opening therein, said electrode wheel, said electrode element and said guide means being located in said housing, said guide means being operative for guiding a needle longitudinally inserted into said needle entry opening so that it passes into engagement with both said electrode wheel and said electrode element; and cartridge means in said housing, said cartridge means including a container portion and a cover portion, said container portion being operative for receiving debris generated through contact with said electrode wheel and said electrode element, said cartridge means being removable from said apparatus, said cartridge means being adapted so that said cover portion is automatically received on said container portion upon removal of said cartridge means form said housing.

21. In the apparatus of claim 20, said container portion having an open upper end and having primary and secondary compartments formed therein, said primary compartment being operative for receiving said debris therein, said cover portion being retracted into said secondary compartment when said cartridge means is in the operative position thereof and substantially covering the upper end of said container portion when said cartridge means is removed from said housing.

22. The apparatus of claim 21, further comprising latch means on said housing for moving said cover portion to a retracted position wherein said cover portion is received in said secondary compartment when said cartridge means is moved to the operative position thereof and for moving said cover portion to a position wherein said cover portion substantially covers the upper end of said container portion when said cartridge means is removed from said housing.

* * * * *